(12) United States Patent
Lynn

(10) Patent No.: US 8,735,337 B2
(45) Date of Patent: *May 27, 2014

(54) AQUEOUS OZONE SOLUTION FOR OZONE CLEANING SYSTEM

(75) Inventor: Daniel W. Lynn, Omaha, NE (US)

(73) Assignee: Food Safety Technology, LLC, Omaha, NE (US)

( * ) Notice: Subject to any disclaimer, the term of this patent is extended or adjusted under 35 U.S.C. 154(b) by 330 days.

This patent is subject to a terminal disclaimer.

(21) Appl. No.: 12/468,952

(22) Filed: May 20, 2009

(65) Prior Publication Data

US 2009/0233839 A1    Sep. 17, 2009

Related U.S. Application Data

(63) Continuation-in-part of application No. 12/047,498, filed on Mar. 13, 2008, now Pat. No. 8,071,526.

(60) Provisional application No. 60/894,476, filed on Mar. 13, 2007.

(51) Int. Cl.
*C11D 3/48* (2006.01)

(52) U.S. Cl.
USPC ........... 510/382; 510/111; 510/218; 510/219; 510/387; 510/393; 210/758; 210/760

(58) Field of Classification Search
USPC ........... 510/111–383, 387, 393; 210/758–780
See application file for complete search history.

(56) References Cited

U.S. PATENT DOCUMENTS

| | | | |
|---|---|---|---|
| 4,035,657 A | 7/1977 | Carlson | |
| 4,176,061 A | 11/1979 | Stopka | |
| 4,352,740 A | 10/1982 | Grader et al. | |
| 4,517,159 A | 5/1985 | Karlson | |
| 4,686,036 A | 8/1987 | Laederach-Zaugg | |
| 4,801,310 A | 1/1989 | Bielefeldt | |
| 4,849,237 A | 7/1989 | Hurst | |
| 4,900,481 A | 2/1990 | Kishioka | |
| 4,963,269 A | 10/1990 | Sasaki et al. | |

(Continued)

FOREIGN PATENT DOCUMENTS

| CA | 2491781 | 7/2005 | |
|---|---|---|---|
| JP | 2003320232 | * 11/2003 | ............... B01F 3/04 |

OTHER PUBLICATIONS

International Search Report and Written Opinion for PCT/US08/56936 dated Jun. 3, 2008 (13 pages).

(Continued)

*Primary Examiner* — Tri V Nguyen

(74) *Attorney, Agent, or Firm* — Polsinelli PC

(57) ABSTRACT

A method of making an aqueous ozone solution for an industrial cleaning system is described. The method includes providing a reaction vessel for entraining ozone gas in an aqueous solution. The reaction vessel includes a conical-shaped surface having a two or more edges or ridges. The conical-shaped surface defines an interior, and two or more edges or ridges are in contact with the interior. The reaction vessel is in fluidic communication with a supply of water. The reaction vessel is in fluidic communication with a supply of a first aqueous ozone solution. The first aqueous ozone solution is directed to the conical-shaped surface. Water is directed to the conical-shaped surface, and the water and the first aqueous ozone solution are mixed to form a second aqueous ozone solution.

14 Claims, 6 Drawing Sheets

(56) References Cited

U.S. PATENT DOCUMENTS

| | | | |
|---|---|---|---|
| 5,069,880 | A | 12/1991 | Karlson |
| 5,174,905 | A | 12/1992 | Shawn |
| 5,186,841 | A | 2/1993 | Schick |
| 5,207,237 | A | 5/1993 | Langford |
| 5,213,773 | A | 5/1993 | Burris |
| 5,236,512 | A | 8/1993 | Rogers et al. |
| 5,411,713 | A | 5/1995 | Iwanaga |
| 5,431,861 | A * | 7/1995 | Nagahiro et al. ......... 261/140.1 |
| 5,493,754 | A | 2/1996 | Gurstein et al. |
| 5,503,808 | A | 4/1996 | Garbutt et al. |
| 5,556,200 | A | 9/1996 | Ekholm et al. |
| 5,641,456 | A | 6/1997 | Rosenauer |
| 5,645,797 | A | 7/1997 | Lo |
| 5,670,094 | A | 9/1997 | Saski et al. |
| 5,720,905 | A | 2/1998 | Ho |
| 5,815,869 | A | 10/1998 | Hopkins |
| 5,816,498 | A | 10/1998 | Smith, Jr. et al. |
| 5,824,243 | A | 10/1998 | Contreras |
| 5,824,274 | A | 10/1998 | Long |
| 5,839,155 | A | 11/1998 | Berglund et al. |
| 5,863,128 | A | 1/1999 | Mazzei |
| 5,865,995 | A | 2/1999 | Nelson |
| 5,914,089 | A | 6/1999 | Murakami et al. |
| 5,951,921 | A | 9/1999 | Koganezawa et al. |
| 6,030,586 | A | 2/2000 | Kuan |
| 6,039,815 | A | 3/2000 | Yeol et al. |
| 6,076,808 | A | 6/2000 | Porter |
| 6,106,731 | A | 8/2000 | Hayes |
| 6,115,862 | A | 9/2000 | Cooper et al. |
| 6,153,151 | A | 11/2000 | Moxley et al. |
| 6,207,064 | B1 | 3/2001 | Gargas |
| 6,250,324 | B1 | 6/2001 | Conrad et al. |
| 6,274,053 | B1 | 8/2001 | Conrad |
| 6,276,304 | B1 | 8/2001 | Tai |
| 6,348,227 | B1 | 2/2002 | Caracciolo |
| 6,361,688 | B1 | 3/2002 | Nelson |
| 6,455,017 | B1 | 9/2002 | Kasting et al. |
| 6,458,257 | B1 | 10/2002 | Andrews et al. |
| 6,458,398 | B1 | 10/2002 | Smith et al. |
| 6,464,210 | B1 | 10/2002 | Teran et al. |
| 6,499,671 | B1 | 12/2002 | Sands et al. |
| 6,517,731 | B2 | 2/2003 | Conrad |
| 6,585,898 | B1 | 7/2003 | Ekberg et al. |
| 6,638,364 | B2 | 10/2003 | Harkins et al. |
| 6,649,052 | B2 | 11/2003 | Lee et al. |
| 6,755,977 | B2 | 6/2004 | Brunsell |
| 6,808,637 | B2 | 10/2004 | Cho |
| 6,817,541 | B2 | 11/2004 | Sands et al. |
| 6,948,504 | B2 | 9/2005 | Fittkau et al. |
| 6,962,654 | B2 | 11/2005 | Arnaud |
| 6,964,739 | B2 | 11/2005 | Boyd et al. |
| 6,991,685 | B2 | 1/2006 | Kravitz et al. |
| 7,022,225 | B1 | 4/2006 | Clawson et al. |
| 7,086,407 | B2 | 8/2006 | Lynn |
| 7,087,123 | B2 | 8/2006 | Lynn |
| 7,087,124 | B2 | 8/2006 | Lynn |
| 7,108,781 | B2 | 9/2006 | Martin |
| 7,188,632 | B2 | 3/2007 | Lynn |
| 7,255,332 | B2 | 8/2007 | Osborn et al. |
| 7,264,006 | B2 | 9/2007 | Fittkau et al. |
| 7,264,680 | B2 | 9/2007 | Gebhart et al. |
| 7,272,947 | B2 | 9/2007 | Anderson et al. |
| 7,275,982 | B1 | 10/2007 | Brandt et al. |
| 7,276,168 | B2 | 10/2007 | Haibara et al. |
| 2003/0049164 | A1 | 3/2003 | Bon et al. |
| 2003/0173309 | A1* | 9/2003 | Kim .............................. 210/760 |
| 2005/0214159 | A1 | 9/2005 | Schwei et al. |
| 2007/0189972 | A1 | 8/2007 | Chiba et al. |
| 2007/0199581 | A1 | 8/2007 | Lynn et al. |
| 2007/0205161 | A1* | 9/2007 | Chiba et al. ................... 210/748 |
| 2007/0286795 | A1 | 12/2007 | Chiba et al. |
| 2008/0227680 | A1 | 9/2008 | Lynn |
| 2009/0008806 | A1 | 1/2009 | Lynn |
| 2009/0032473 | A1 | 2/2009 | Ueki et al. |
| 2009/0120473 | A1 | 5/2009 | Lynn |
| 2009/0233839 | A1 | 9/2009 | Lynn |
| 2010/0010422 | A1* | 1/2010 | Watanabe ....................... 604/24 |
| 2010/0021598 | A1 | 1/2010 | Lynn |

OTHER PUBLICATIONS

Trevor C. Suslow, Oxidation Reduction Potential (ORP) for Water Disinfection Monitoring, Control and Documentation, University of California, Division of Agriculture and Natural Resources, 2004 (5 pages).

Office Action for U.S. Appl. No. 12/047,498 dated Aug. 31, 2010 (13 pages).

Office Action for U.S. Appl. No. 12/179,335 dated Nov. 23, 2011 (12 pages).

Office Action for U.S. Appl. No. 12/179,335 dated Jun. 7, 2012 (11 pages).

International Search Report and Written Opinion for PCT/US11/39711 dated Oct. 5, 2011 (9 pages).

International Search Report and Written Opinion for PCT/US2011/039756 dated Dec. 2, 2011 (11 pages).

U.S. Appl. No. 13/310,108 Office Action mailed Sep. 25, 2013 (12 pages).

* cited by examiner derlying U.S. Pat. No. 8,735,337 B2

AQUEOUS OZONE SOLUTION FOR OZONE CLEANING SYSTEM

RELATED APPLICATIONS

This application is a continuation in part of U.S. patent application Ser. No. 12/047,498, filed Mar. 13, 2008 now U.S. Pat. No. 8,071,526, which claims the benefit of U.S. Provisional Application No. 60/894,476 filed on Mar. 13, 2007. The disclosure of U.S. patent application Ser. No. 12/047,442, titled Ozone Cleaning System, filed Mar. 13, 2008, invented by Daniel W. Lynn, is hereby incorporated by reference in its entirety. The disclosure of U.S. patent application Ser. No. 12/047,461, titled Reaction Vessel for an Ozone Cleaning System, filed Mar. 13, 2008 now U.S. Pat. No. 8,075,705, invented by Daniel W. Lynn, is hereby incorporated by reference in its entirety.

FIELD OF INVENTION

The present invention relates to an aqueous ozone solution for ozone cleaning systems.

BACKGROUND OF INVENTION

Ozone in a solution has been previously used for cleaning and sanitizing. Maintaining a solution with a consistent ozone concentration has proven difficult. Ozone is unstable, which provides for it cleaning and sanitizing capabilities, but also makes consistent ozone levels difficult to maintain in a solution. If the ozone solution has too much ozone or large bubbles of ozone, then off-gassing problems may occur, as the excess ozone is released into the work facility creating environmental problems and possible violating workplace safety regulations. If the solution has too little ozone, then the cleaning and sterilizing may not be as effective as desired.

Other systems utilize a spraying device that simultaneously sprays two separate streams of water and an ozone solution. The stream of water is applied at high pressure for removing particles and the ozone solution is applied for sanitizing.

Ozone solutions have proven difficult to consistently and uniformly prepare in sufficient quantities required for industrial cleaning applications.

SUMMARY OF INVENTION

A method of making an aqueous ozone solution for an industrial cleaning system is described. Compositions for aqueous ozone solutions for use with industrial cleaning system are also described. The aqueous ozone solutions serve as a cleaning and sterilizing agent. Systems for making and applying the aqueous ozone solutions are also described.

In one embodiment, the method of making the aqueous ozone solution for the industrial cleaning system includes providing a reaction vessel for entraining ozone gas in an aqueous solution. The reaction vessel includes a conical-shaped surface having a plurality of edges or ridges. The conical-shaped surface defines an interior, and the plurality of edges or ridges are in contact with the interior. The reaction vessel is in fluidic communication with a supply of water. The reaction vessel is also in fluidic communication with a supply of a first aqueous ozone solution. The first aqueous ozone solution is directed to the conical-shaped surface. Water is directed to the conical-shaped surface, and the water and the first aqueous ozone solution are mixed to form a second aqueous ozone solution.

In one embodiment, the aqueous ozone solution comprises approximately 1 part by volume water mixed with approximately 4 parts by volume to approximately 9 parts by volume of a first aqueous ozone solution to form a second aqueous ozone solution that has an oxidation reaction potential of up to approximately 2.6, wherein the second aqueous ozone solution has an ozone concentration of up to approximately 20 ppm, wherein the second ozone solution has less ozone gas bubbles than the first aqueous ozone solution.

The first aqueous ozone solution is mixed with water in the reaction vessel. The reaction vessel reduces the bubbles of ozone gas in the aqueous ozone solution and entrains the remaining bubbles of ozone gas in the aqueous ozone solution to increase the oxidation reduction potential of the aqueous ozone solution.

The reaction vessel includes the conical-shaped surface having the plurality of edges or ridges. An inlet port is in fluidic communication with the supply of the first aqueous ozone solution to supply the first aqueous ozone solution to the conical-shaped surface. Nozzles are in fluidic communication with the supply of water, and the nozzles direct the water under pressure at the conical-shaped surface, and the water mixes with the first aqueous ozone solution from the inlet port. An outlet is in fluidic communication with the industrial cleaning system. The reaction vessel may receive the first aqueous ozone solution from an injector.

The aqueous ozone solution is applied to attack and destroy pathogens and to act as a no-rinse sanitizer for hard surfaces in a variety of applications, especially for industrial cleaning applications in facilities related to food processing. The aqueous ozone solution may be used for many different sanitation applications in many different industries and facilities. For example, the aqueous ozone solution may be used in cosmetic manufacturing facilities, hospitals, fast food outlets, individual homes, etc. The aqueous ozone solution may be used with a variety of different "clean in place" systems, such as, for example, water-bottling facilities and equipment, breweries and brewing equipment, ethanol processing facilities, snack food processing facilities, cooling towers, etc. The use of the aqueous ozone solution is not limited to any particular type of industry or application type.

In the methods described herein, ozone gas is entrained into water, forming the first aqueous ozone solution, which is delivered to the to the reaction vessel for further entraining and concentrating of the ozone gas into the aqueous ozone solution. Water is mixed with the first aqueous ozone solution to form the second aqueous ozone solution.

In the methods described herein, an ozone generator produces ozone gas. The ozone generator directs the ozone gas to the injector, which is also in communication with a supply of water. The injector injects ozone gas from the ozone generator into the water from the supply of water to form the first aqueous ozone solution. The reaction vessel receives the first aqueous ozone solution from the injector and additional water from the water supply. The reaction vessel comprises the conical-shaped vessel having the plurality of edges or ridges for reducing a bubble size of the ozone gas in the first aqueous ozone solution and for mixing the water with the first aqueous ozone solution to form the second aqueous ozone solution. A pump in communication with the reaction vessel distributes the second aqueous ozone solution to the hard surfaces for cleaning the hard surfaces.

The reaction vessel reduces the amount of bubbles and the bubble size of the ozone gas in the first and second aqueous ozone solutions, which allows for the system to produce an aqueous ozone solution with a greater concentration of ozone gas and a higher oxidation reduction potential. Since the bubbles of ozone are smaller and fewer than the bubbles of ozone in a typical ozone solution, the aqueous ozone solution contains a greater amount of ozone and has the higher oxidation reduction potential. This provides for a more effective cleaning and sanitizing system.

The hard surfaces may include, for example, conveyor systems, processing equipment, floors, tables, etc. The solution of aqueous ozone may be applied at a high pressure to the hard surfaces, and is effective for sanitizing the hard surfaces and removing soils and bulk materials from the hard surfaces. When applied at high pressure, the solution penetrates and destroys the soils and oxides of a biofilm that acts as the bond or glue that allows the soils and oxides to attach themselves to the hard surfaces.

The methods and solution may be used in the system described herein. The system is a chemical-free system that destroys the biofilm on hard surfaces during food processing production in food processing facilities. The system allows for continuous or extended production in the facility. When installed in processing facilities, the hard surfaces can be maintained 24 hours a day, 7 days a week accomplishing both a microbial reduction as well as improving aesthetics. The system allows the plant to do mid-shift sanitation or a cleaning application that the plant could not do with present conventional systems (because ozone is approved by the Food and Drug Administration for direct food contact and chemicals are not).

The aqueous ozone solution assists in providing a chemical-free, high pressure cleaning system that replaces present conventional cleaning systems. The use of the aqueous ozone solution reduces the need for chemicals, hot water, and labor. As such, the processor's operating costs may be reduced by 50%. Conventional cleaning systems often require the use of warm or hot water, which may form condensation on the hard surfaces. The condensation may provide for or encourage the growth of microbes. Because the system only uses cold water, condensation is not likely to form on the hard surfaces. The system also reduces the hydraulic load on the waste-water treatment system and eliminates the need to treat the chemicals that would be present in conventional wastewater discharge streams.

Ozone gas is generally unstable (a property that gives ozone its extraordinary oxidizing capabilities). Ozone gas cannot be packaged or stored and must be generated on site. The system includes an on-site ozone generator combined with an air preparation unit and the injector to safely get the ozone into the water. As such, the system requires no drums to store ozone, records and reports relating to the drums, or disposal concerns relating to the drums.

The use of ozone as cleaning and sterilizing agent is a chemical treatment like other oxidizers, including chlorine, potassium permanganate, hydrogen peroxide, etc. Ozone's extraordinary speed and power sets ozone apart from the other oxidizers, but there are rules to be followed in its application. Stoichiometric (chemical value) calculation charts and formulas are readily available for all common inorganic contaminants, including but not limited to, iron, manganese, sulfide compounds. Simple formulas for flow and contaminant loading make ozone generator sizing easy. With contact times in the 2-6 minute range for common contaminants, instead of the 20-30 minute times associated with chlorination, the system described herein is simpler, more compact and efficient than traditional cleaning treatments.

DETAILED DESCRIPTION OF PREFERRED EMBODIMENTS

Figure 1:
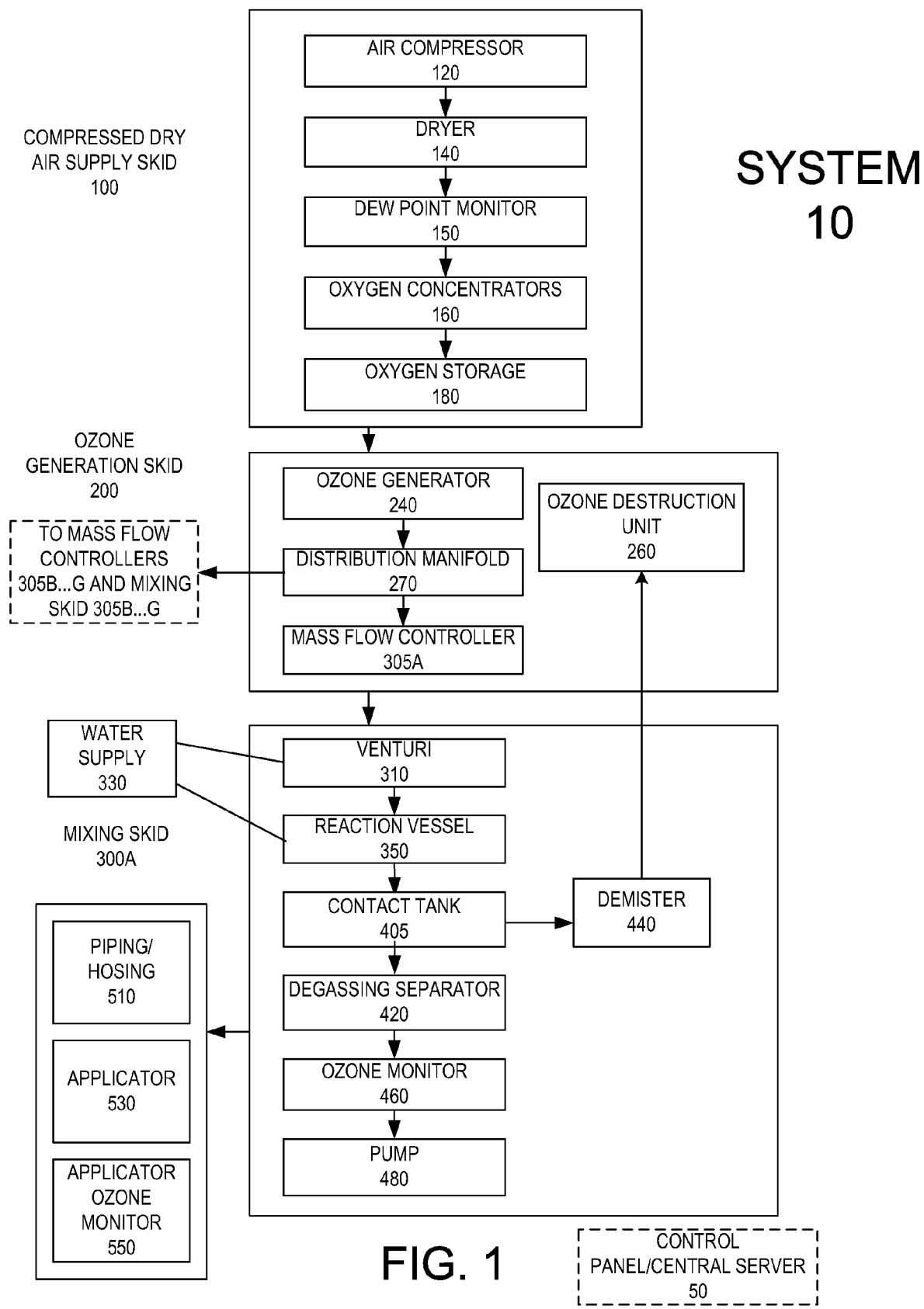
FIG. 1 shows a process flow diagram of the ozone cleaning system that produces and distributes the aqueous solution of ozone

The methods described herein reduce the bubble size of ozone gas in the aqueous ozone solution and the number of bubbles in the aqueous ozone solution. The methods increases the concentration of ozone in the aqueous ozone solution as well as its oxidation reduction potential to improve the cleaning and sanitizing capabilities of the aqueous ozone solution. The compositions of aqueous ozone solution described herein have less bubbles and smaller bubbles of ozone gas than conventional solutions. Decreasing the bubble size of the ozone gas also assists in maintaining a uniform concentration of ozone gas in the aqueous ozone solution and reducing off-gassing. The compositions of aqueous ozone solution provide for cleaning and sanitizing of industrial facilities.

Fresh water and the first aqueous ozone solution are mixed to form the second aqueous ozone solution. The reaction vessel 350 circulates the fresh water and forms a vortex, which mixes with the first aqueous ozone solution. The mixing in the reaction vessel 350 of the water and the first aqueous ozone solution breaks the ozone gas bubbles in the first aqueous ozone solution into smaller and smaller bubbles and forms the second aqueous ozone solution that exits the reaction vessel 350. In reaction vessel 350, the first aqueous ozone solution is forced into a saturated aqueous ozone solution having an ozone concentration of up to approximately 20 ppm and an oxidation reaction potential of up to approximately 2.6. Off-gassing of ozone gas is reduced by the reaction vessel 350, as many of the gas bubbles in the first aqueous ozone solution are crushed.

As described in greater detail below, the reaction vessel 350 is in fluidic communication with a supply of the first aqueous ozone solution, e.g., a venturi 310, in which the first aqueous ozone solution is formed by injection of ozone gas into water in the venturi 310. The reaction vessel 350 is also in fluidic communication with a supply of water 330 for mixing with the first aqueous ozone solution. After the mixing in the reaction vessel 350, the reaction vessel 350 outputs the second aqueous ozone solution to a contact tank 405.

As described in greater detail below, the reaction vessel 350 comprises a conical-shaped surface 385 having a plurality of edges 380 on the conical-shaped surface 385. The conical-shaped surface 385 imparts a rotating action or a vortex to the water entering the reaction vessel 350 from the supply of water 330, and the water rotates about the conical-shaped surface 385 toward the first aqueous ozone solution entering the reaction vessel 350, which crushes ozone gas bubbles in the first aqueous ozone water solution.

The system 10 provides a centralized system for producing an aqueous ozone solution, i.e., the aqueous ozone solution is prepared and distributed from a central location in an industrial facility to different application points throughout the industrial facility. The system 10 provides for the distribution of the aqueous ozone solution at different flow rates and at different concentrations to the different application points. The system 10 monitors and maintains the ozone concentration and flow rate of the aqueous ozone solution at desired levels. The system 10 provides a uniform and consistent aqueous ozone solution without off-gassing problems. Fluctuations in the concentration of ozone in the aqueous ozone solution are kept to a minimum with the aid of monitoring systems that monitor the concentration of ozone in the aqueous ozone solution and modulate levels of ozone gas introduced into the aqueous ozone solution. The system 10 increases the oxidation reaction potential of a conventional aqueous ozone solution by reducing the bubble size of ozone gas and minimizing the amount of bubbles of ozone in the aqueous ozone solution.

A process flow diagram for the system is shown in FIG. 1. A control panel/central server 50 comprising a programmable logic controller and user interface is in electrical communication with the components of the system 10 to operate, monitor, and direct the system 10. The control panel/central server 50 regulates the concentration of ozone in the ozonated water solution and the flow of ozonated water solution. The control panel/central server 50 is in electrical communication with the various components, systems and assemblies of the system 10 to ensure that the desired flow and concentration of the ozonated water solution are maintained. The control panel/central server 50 regulates the flow and amount of ozone gas that is entrained in the solution. The system 10 produces high pressure and high volumes of the ozonated water solution to clean and sanitize industrial facilities. The system 10 may be scaled depending upon the application, for example, the system 10 may provide lower volumes, e.g. 1 gallon per minute and higher volumes, e.g., 10,000 gallons per minute.

Ozone gas for use with the system 10 is produced from ambient air. An important feature of the system 10 is that it ensures that a consistent supply of dried air is delivered to oxygen concentrators 160, which produce essentially pure oxygen gas for ozone generation in ozone generators 240, such that the system 10 provides a sufficient quantity of ozone gas with consistent quality. The consistent supply of dried air ultimately assists in creating the consistent supply of the aqueous ozonated solution produced by the system 10.

Figure 3:
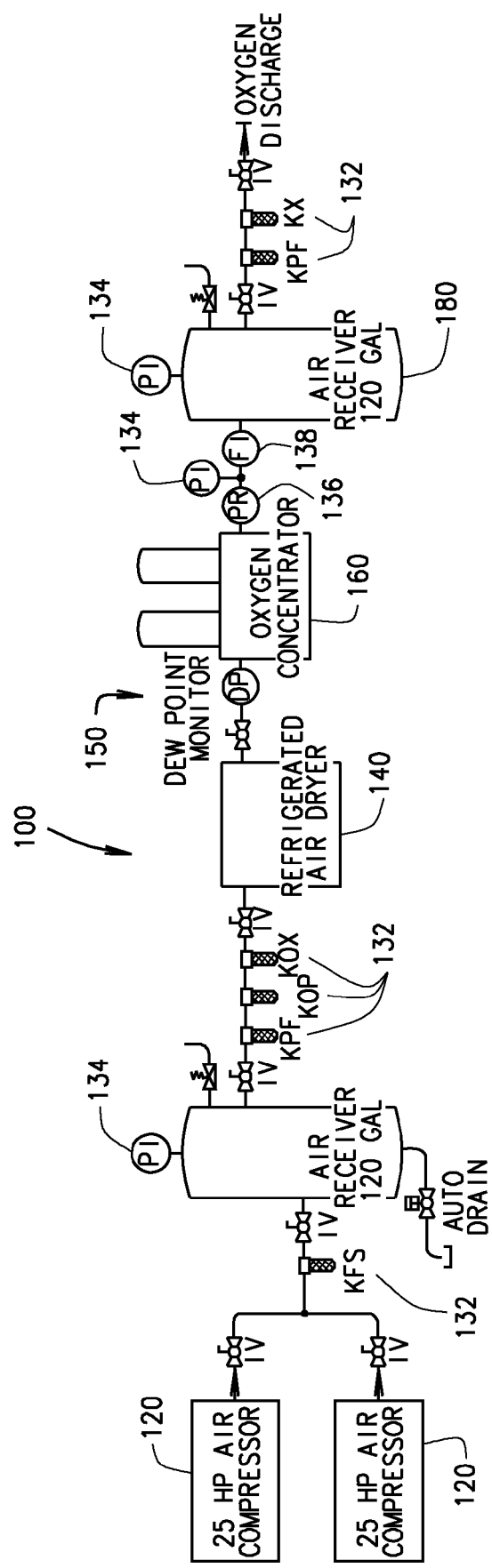
FIG. 3 shows a view of the compressed dry air supply skid.

The system 10 draws in the ambient air to a compressed dry air supply skid 100 (shown in FIG. 3) comprising an air compressor 120, a dryer 140, a dew point monitor 150, the oxygen concentrators 160, and an oxygen storage tank 180. The air compressor 120 is in communication with the dryer 140. The air compressor 120 compresses the ambient air and delivers the compressed air to the dryer 140. The compressed air is dried in the dryer 140. The dryer 140 is in communication with the dew point monitor 150, which measures the dew point of air exiting the dryer 140. A suitable dew point monitor 150 is commercially available from Vaisala Instruments.

From the dew point monitor 150, the compressed and dried air passes to the oxygen concentrators 160, which produce essentially pure oxygen gas from the dried and compressed air that is stored in the oxygen storage tank 180. The oxygen storage tank 180 acts as a storage and supply reservoir of oxygen for ozone generation. Excess oxygen is stored in the oxygen storage tank.

Maintaining a high concentration of oxygen in the oxygen gas assists in creating the consistent supply of the aqueous ozonated solution produced by the system 10. Generally, the essentially pure oxygen gas will contain over 90% pure oxygen, with a preferred range of approximately 95% to 98% pure oxygen. The oxygen concentrators 160 may use a pressure swing adsorption process using a molecular sieve. A suitable oxygen concentrator 160 is commercially available from the AirSep Corporation. The compressed dry air supply skid 100 may further include one or more filters 132 for oil and contaminant removal, one or more pressure indicators 134 for monitoring the pressures of the compressed air and the stored oxygen gas in the oxygen storage tank 180, and one or more pressure relief valves 136 for discharging pressurized gas. A flow controller 138 modulates the flow of oxygen gas from the oxygen concentrators 160 to the oxygen storage tank 180, while one of the pressure indicators 134 and one of the pressure relief valves 136 is also employed to monitor and provide pressure relief for the oxygen gas directed to the oxygen storage tank 180 from the oxygen concentrators 160.

The essentially pure oxygen gas is delivered to an ozone generation skid 200 (shown in FIG. 4) comprising the ozone generator 240, an ozone destruct unit 260, a distribution manifold 270, and one or more mass flow controllers 305. The ozone generation skid produces ozone and directs it via the distribution manifold 270 and the one or more mass flow controllers 305 to one or more mixing skids 300 (shown in FIG. 5).

The ozone generator 240 produces ozone gas from the essentially pure oxygen gas. The ozone generator 240 is in communication with the oxygen storage tank 180. The ozone generator 240 is configured with a cooling system, such as a cool-water recirculation jacket 243, to maintain the ozone generator 240 at under approximately 100° F. The ozone generator may utilize a corona discharge method of ozone generation. Maintaining a cool temperature is preferred to regulate ozone concentration, as higher concentrations of ozone gas are achieved from the ozone generator 240 when the temperature of the ozone generator 240 is maintained at these cool levels. The ozone destruct unit 260 receives excess ozone or ozone that has separated from the aqueous ozone solution in other parts of the system 10 for destruction.

Figure 4:
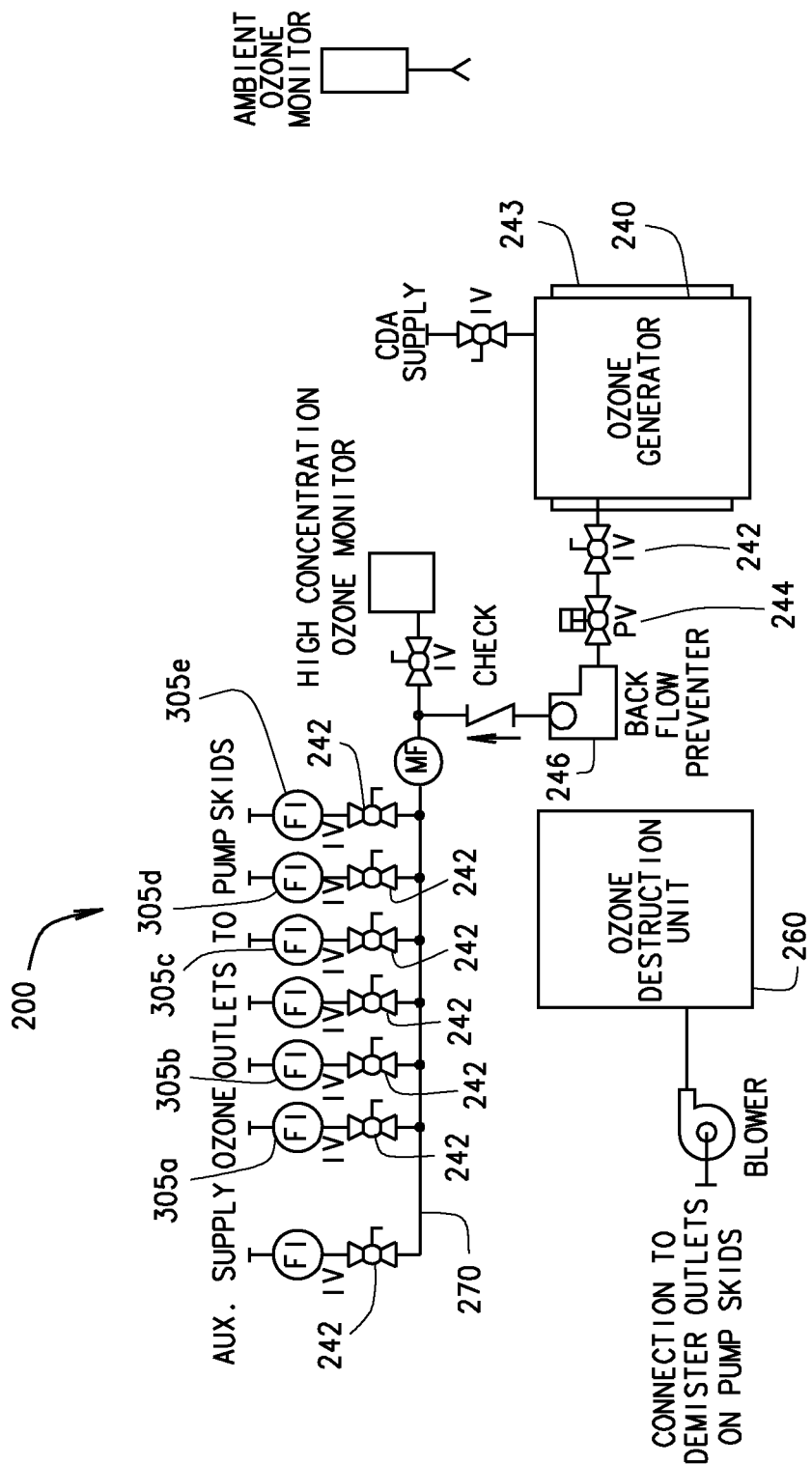
FIG. 4 shows a view of the ozone generation skid.

As shown in FIG. 4, the ozone generation skid 200 comprises one or more ozone generators 240. Some of the one or more ozone generators may only be used in a backup capacity, i.e., when one of the previously operational ozone generators 240 require maintenance or breaks-down. As such, the industrial facility will not need to shut down for a conventional cleaning process when one of the ozone generators 240 is non-operational. Depending on the overall size of the system 10, up to 30 or more ozone generators 240 may be included in the ozone generation skid 200. The ozone generators 240 are in electrical communication with the control panel/central server 50 in order to monitor and control their operation.

The ozone generation skid 200 includes the distribution manifold 270 and the mass flow controllers 305 for disseminating the ozone gas to the one or more mixing skids 300 for mixing with water to produce the aqueous ozone solution. The distribution manifold 270 is in communication with the ozone generators 240. An isolation valve 242, an air actuated ball valve 244, and a back flow preventer 246 are positioned between the ozone generator 240 and the distribution manifold 270 to direct the flow of ozone gas from the ozone generator 240 to the distribution manifold 270.

The mass flow controllers 305 are in electrical communication with the control panel/central server 50 for modulating the flow of the ozone gas. A suitable mass flow controller 305 is commercially available from Eldrige, Products, Inc.

Typically, the distribution manifold 270 will branch into separate lines each having a mass flow controller 305a-g in communication with each of the one or more mixing skids 300a-g. Additional isolation valves 242 are configured between the mass flow controllers 305a-g and the distribution manifold 270. The number of mixing skids 300a-g and mass flow controllers 305a-g will depend upon the application requirements of the system 10. For example, certain industrial facilities may only require two to four mixing skids 300a-g and mass flow controllers 305a-g, while other industrial facilities may require six to eight mixing skids 300a-g and mass flow controllers 305a-g. The distribution manifold 270 further directs ozone gas to an auxiliary use, such as a deodorizer, or to the ozone destruction unit 260.

Figure 5:
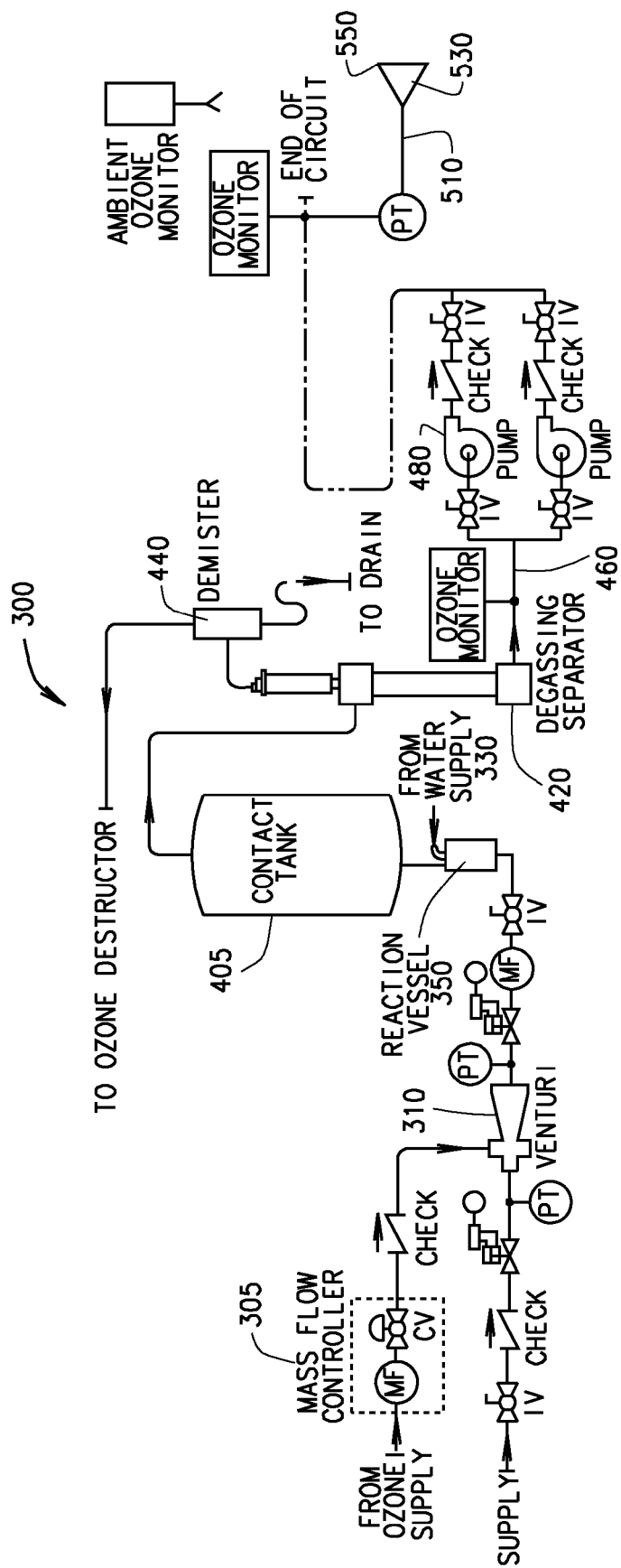
FIG. 5 shows a view of the mixing skid.
Figure 6:
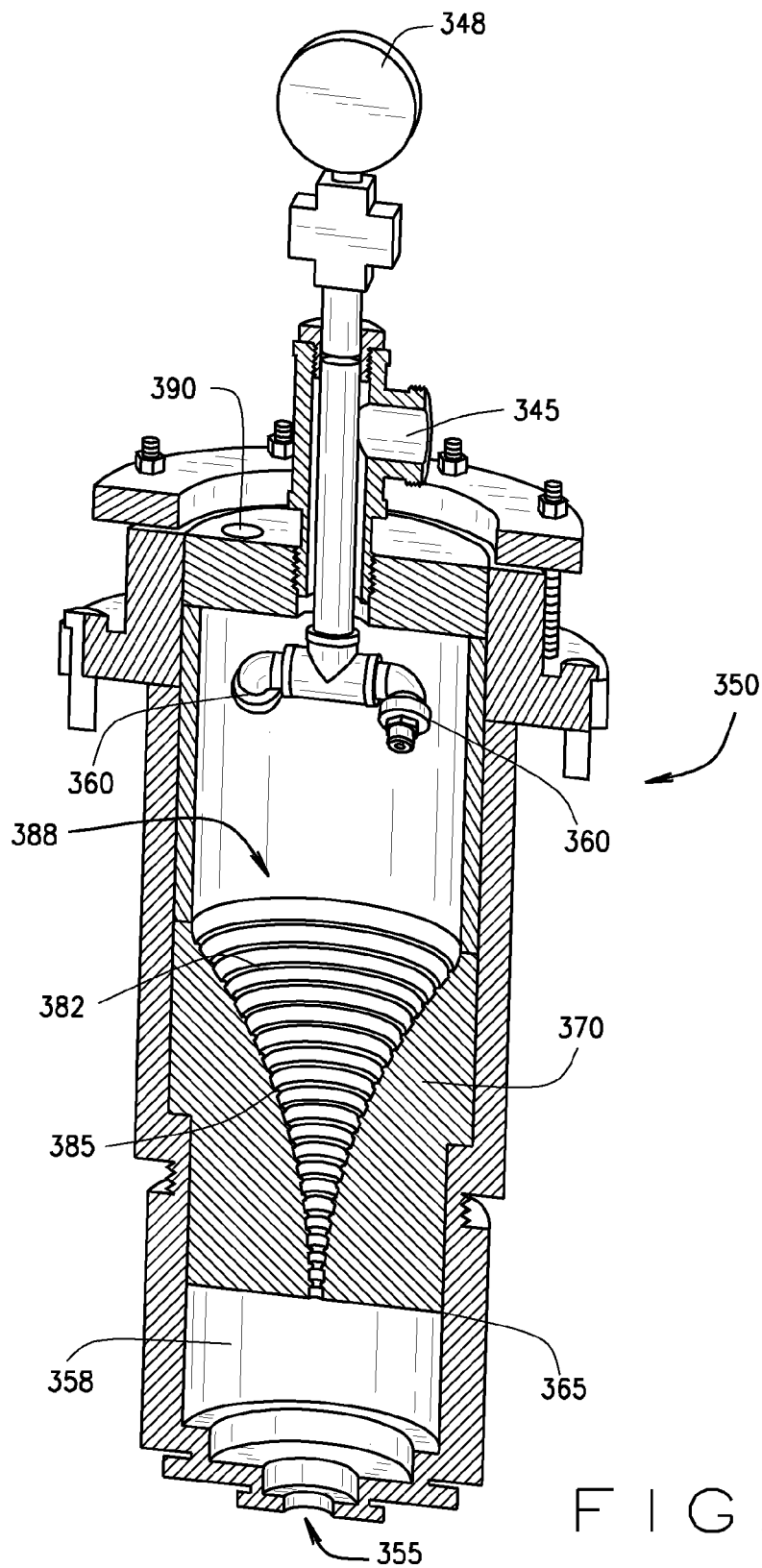
FIG. 6 shows an alternative view of the reaction vessel.

As shown in FIG. 5, the one or more mixing skids 300 comprise the venturi 310, the reaction vessel 350, the contact tank 405, a degassing separator 420, a demister 440, a mixing ozone monitor 460, and a pump 480. At the mixing skids 300, water from the water supply 330 and ozone gas from the ozone generation skid 200 are directed via lines, hoses, and/or piping to the venturi 310 for forming the first aqueous ozone solution. The venturi 310 acts as an injector, i.e., it injects the ozone gas into the water. A preferred injector is commercially available from the Mazzei Injector Corporation; however, any of a variety of injectors could be utilized in the one or more mixing skids 300.

As previously noted, before reaching the venturi 310, the ozone gas passes through the one or more mass flow controllers 305a-g, which measures the flow of ozone to the venturi 310 and modulates the flow of ozone to the venturi 310. The mass flow controllers 305a-g are in electrical communication with the control panel/central server 50 in order regulate and control the flow of ozone gas through the mass flow controllers 305a-g. The operator of the system may adjust the flow of ozone to the venturi 310 to obtain the desired ozone concentrations level in the aqueous ozone solution.

Although the first aqueous ozone solution has now been formed by the venturi 310, the first aqueous ozone solution is now directed to the reaction vessel 350 for further processing to reduce the bubble size of the ozone gas in the aqueous ozone solution and the number of bubbles and to increase the concentration of ozone in the aqueous ozone solution as well as its oxidation reduction potential. Decreasing the bubble size of the ozone gas also assists in maintaining a uniform concentration of ozone gas in the aqueous ozone solution. A supply of water is in communication with the reaction vessel 350. The supply of water directs water to a conical-shaped surface 385 of the reaction vessel 350, and the water mixes with the first aqueous ozone solution to form the second aqueous ozone solution.

The operation and structure of the reaction vessel 350 will now be described in detail with reference to FIG. 2. The first aqueous ozone solution from the venturi 310 is discharged into the bottom of reaction vessel 350 at an inlet port 355. The first aqueous ozone solution travels up an inner vortex assembly sleeve 370 in the interior of the reaction vessel 350.

Nozzles 360 discharge a stream of fresh water, at approximately 50 to 55 psi, at the top of the reaction vessel 350 into the inner vortex assembly sleeve 370. The fresh water from the nozzles 360 dilutes the first aqueous ozone solution from the venturi 310. The nozzles 360 receive the fresh water from the water supply 330 through a fresh water inlet 345 and a regulator 348. The regulator 348 is in electrical communication with the control panel/central server 50. The regulator 348 provides pressure readings to the control panel/central server 50, and the regulator 348 modulates the pressure and flow of fresh water into the inner vortex assembly sleeve 370 at the direction of the control panel/central server 50.

Figure 2:
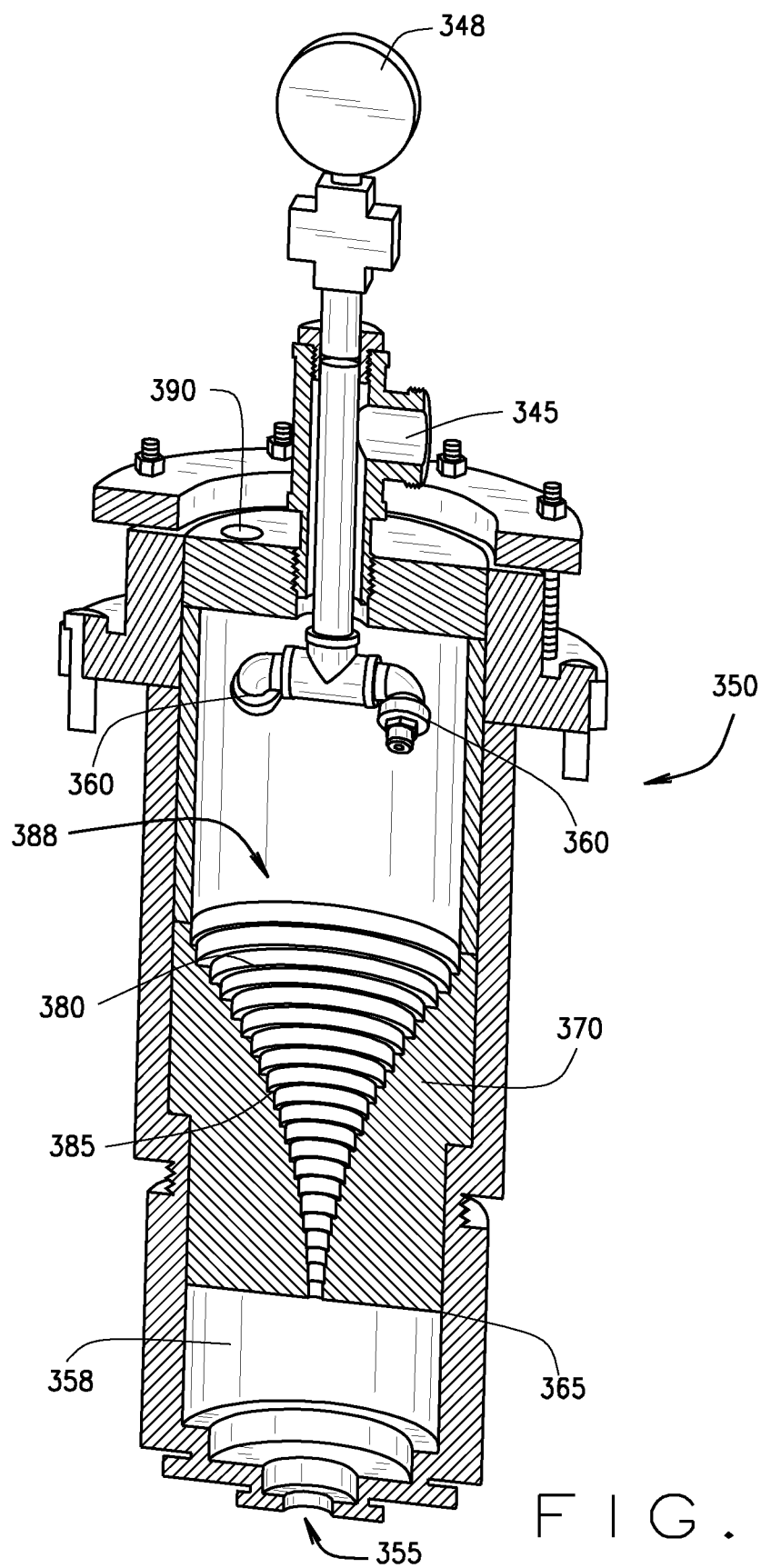
FIG. 2 shows a sectional view of the reaction vessel.

The inner vortex assembly sleeve 370 is shown in FIG. 2. The inner vortex assembly sleeve 370 is under a pressure of approximately 50 psi to approximately 125 psi. The pressure in the inner vortex assembly sleeve 370 is varied to accommodate the desired flow rate of the aqueous ozonated water solution from the particular mixing skid 300 a-g. If the pressure in the inner vortex assembly sleeve 370 is too high, then off-gassing problems of ozone gas may occur.

The inner vortex assembly sleeve 370 comprises the conical-shaped surface 385. The first aqueous ozone solution enters the bottom of the reaction vessel 350 at the inlet port 355, while fresh water is discharged from nozzles 360 toward the entering first aqueous ozone solution.

From the inlet port 355, the first aqueous ozone solution enters a cavity 358, which acts as a reservoir to receive the first aqueous ozone solution. An opening 365 separates the conical-shaped surface 385 from the cavity 358. The opening 365 is in fluidic communication with the cavity 358 and the inner vortex assembly sleeve 370. The inner vortex assembly sleeve 370 has a narrow diameter toward the inlet port 355 and the opening 365 and gradually increases in diameter toward an outlet 390, which creates the conical-shaped surface 385. The opening 365 is at the narrowest point of the conical-shaped surface 385.

The nozzles 360 direct the fresh water at the conical-shaped surface 385. Specifically, the nozzles 360 direct the fresh water at the sloping surfaces of the conical-shaped surface 385. The conical-shaped surface has sloping surfaces or sides leading to the opening 365. The direction of the nozzles 360 and the conical-shaped surface 385 imparts a rotating action or a vortex to the fresh water, and the fresh water rotates about the conical-shaped surface 385 toward the opening 365. As such, fresh water from the nozzles 360 moves down the conical-shaped surface 385 in the rotating manner, under centrifugal force, which crushes ozone gas bubbles in the first aqueous ozone water solution entering the inner vortex assembly sleeve 370 through the opening 365 from the cavity 358 and crushes ozone gas bubbles in the first aqueous ozone water solution in the cavity 358. As such, the second aqueous ozone solution is formed by mixing the water with the first aqueous ozone solution.

At the opening 365, some of the rotating fresh water from the nozzles 360 may enter the cavity 358. Ozone gas from the aqueous ozone solutions may diffuse with the fresh water in the cavity 358 and at the opening 365. At the opening 365, the first aqueous ozone solution from the cavity 358 passes into a cone void 388, which is the generally hollow central region of the inner vortex assembly sleeve 370, as defined by the conical-shaped surface 385.

The inner vortex assembly sleeve 370 comprises approximately 10 to approximately 50 of the edges 380 on the conical-shaped surface 385. Each of the edges 380 may comprise a generally perpendicular angle above and below the adjacent edge 380. The edges 380 form a stair-step like surface for the conical-shaped surface 385. The edges 380 surround a perimeter of the cone void 388. The edges 380 are in contact with the hollow interior, i.e., the cone void 388. Other constructions, geometries, or surfaces on the conical-shaped surface 385 may be employed to reduce the bubble size of the ozone gas. For example, the conical-shaped surface may include a plurality of concentric ridges 382 on or about the conical-shaped surface 385.

The inner vortex assembly sleeve 370 turns the first aqueous ozone solution, under high pressure, around and against the series of edges 380 or ridges 382 on the interior conical-shaped surface 385 of the inner vortex assembly sleeve 370. The interaction of the fresh water, the first aqueous ozone solution, and the edges 380 crush and break the ozone gas into smaller and smaller bubbles in the aqueous ozone solution, which exits the reaction vessel 350 as the second aqueous solution at the outlet 390. Off-gassing of ozone gas into the cone void 388 is re-mixed into the aqueous ozone solutions. The conical-shaped surface 385 and discharge of fresh water from the nozzles 360 causes the fresh water to circulate and form a vortex which mixes with the first aqueous ozone solution passing through the inner vortex assembly sleeve 370 and eventually exiting at the outlet 390 as the second aqueous solution.

The sleeve 370 is significant to cause the necessary break down of the microscopic bubbles of ozone gas and allows the maximum molar absorptivity of the ozone gas into the second aqueous solution. The aqueous ozone solution is forced into a saturated aqueous ozone solution having an ozone concentration of up to approximately 20 ppm and an oxidation reaction potential of up to approximately 2.6. Breaking down the bubbles of ozone into smaller bubbles of ozone increases the oxidation reduction potential of the ozone in the aqueous ozone solution. The greater oxidation reduction potential of the aqueous ozone solution water allows the ozone to act not only as a sanitizer, but as a degreaser and therefore has more oxidizing power than conventionally mixed solutions. Typically, the aqueous ozone solution entering the reaction vessel 350 at the inlet port 355 and the fresh water entering the reaction vessel forms a solution that is approximately 10% to approximately 20% fresh water, i.e., approximately 1 part by volume fresh water from the water supply is mixed with approximately 4 parts to approximately 9 parts by volume aqueous ozone solution from the inlet port 355. However, due to the crushing of the ozone bubbles in the reaction vessel 350, the ORP value for the aqueous ozone solution exiting the outlet 390 is approximately the same as the ORP value for the aqueous ozone solution entering the inlet 355, despite the dilution of the aqueous ozone solution entering the inlet 355 by the fresh water from the nozzles 360.

The reaction vessel 350 and the inner vortex assembly sleeve may be made from stainless steel, metal alloys, or hard plastic materials, such as chlorinated Polyvinyl Chloride (CPVC).

From the outlet port 390 of the reaction vessel 350, the aqueous ozone solution is directed to the contact tank 405 and a degassing separator 420 in communication with the reaction vessel 350. The contact tank 405 should have a volume approximately twice the desired amount of volume of aqueous ozone solution. For example, if the mixing skid 300a is providing 100 gallons/per minute in flow, then the contact tank 405 should have a capacity of approximately 200 gallons. As such, in this particular example, the solution is spending approximately two minutes in the contact tank 405.

Large gas bubbles are separated from the aqueous ozone solution in the degassing separator 420. The degassing separator is important to remove the excess ozone bubbles from the aqueous ozone solution to reduce the levels of free ozone gas released at an application point during the spraying of the aqueous ozone solution, which in high concentrations could breach OSHA regulations. The separated gas bubbles are directed to a demister 440, where a liquid component of the separated gas bubble is collected and drained, while an ozone gas component of the separated gas bubbles is directed from the demister 440 to the ozone destruction unit 260.

The aqueous ozone solution exiting the degassing separator 420 passes through and the mixing ozone monitor 460 and on to one or more pumps 480 via piping, hosing and/or lines. Depending upon the cleaning and sanitizing application of the system 10, the aqueous ozone solution may be directed to one or more of the pumps 480 which may pump the aqueous ozone solution at different flow rates and pressures from the mixing skid 300. The aqueous ozone solution is pumped from the mixing skid 300 via distribution piping/hosing 510 in communication with the pumps 480 to one or more applicators 530 for applying the aqueous ozone solution to the hard surfaces and other items for sanitation. The applicators 530 include spray wands, nozzles, brushes, nebulizers, spray guns and the like, and various combinations thereof. Each applicator 530 includes an applicator ozone monitor 550.

The concentration of the aqueous ozone solution is monitored by the applicator ozone monitor 550, which measures the exact concentration of ozone in the aqueous ozone solution exiting from the applicator 530. The plant operator may monitor and adjust the concentration of ozone in the aqueous ozone solution based on readings from the applicator ozone monitor 550.

The applicator ozone monitor 550 is in electrical communication with the control panel/central server 50. If the applicator ozone monitor 550 indicates that the levels of ozone in the aqueous ozone solution are too low, then the operator or automated systems in the control panel/central server 50 may adjust the mass flow controller 305 to increase the amount of ozone gas directed to the venturi 310, such that concentration levels of ozone in the aqueous ozone solution at the applicator ozone monitor 550 are increased.

The system 10 may comprise one or mixing skids 300 with one or more pumps 480 supplying one or more applicators 530. The one or more pumps 480 may pump the aqueous ozone solution at different rates and at different concentrations to the different applicators 530. The system 10 may be customized, depending upon a specific industrial facility and its specific cleaning needs. For example, the system 10 may comprise a variety of high pressure and low pressure applicators 530 and with certain applicators applying different concentrations of aqueous ozone solution. The system 10 provides an applied dosage of an aqueous ozone solution that is consistent over time in terms of the desired concentration and flow rate to the one or more applicators 530. The control panel/central server 50, in conjunction with the applicator ozone monitor 550 and mass flow controllers 305, monitor and regulate the concentration and flow of the aqueous ozone solution.

The reaction vessel 350 is important to the mass transfer of ozone gas in the water, i.e., how the ozone gas is dissolved into the water to form the aqueous ozone solution. The system 10 produces a saturated aqueous ozone solution having an ozone concentration of up to approximately 20 ppm.

The reaction vessel 350 helps reduce the number of bubbles and create the smallest possible bubbles of ozone in the second aqueous ozone solution in order to produce the saturated aqueous ozone solution with an ozone concentration of up to approximately 20 ppm and an oxidation reduction potential of 2.6. The amount of ozone dissolved into the water depends, in part, on the surface area of the gas/water interaction. The smaller the bubble, the better the mass transfer because one cubic inch of tiny bubbles has much more surface area than a single, one cubic inch bubble.

The edges 380 on the inner vortex assembly sleeve 370 assist in physically reducing the bubble size of the ozone gas. As the aqueous ozone solution is forced through the inner vortex assembly sleeve 370, the bubbles of ozone contact the edges 380 and break into smaller and smaller bubbles. The smaller bubbles dissolving in the water help to saturate the aqueous ozone solution with ozone.

The pressure, of approximately 50 psi to approximately 125 psi, applied in the reaction vessel 350 also improves the mass transfer between the bubbles of ozone gas and the water. The higher the pressure, the more a "squeeze" is put on the transfer of gas bubbles into the water enhancing the process of dissolving the gas bubbles into the aqueous ozone solution and creating the saturated aqueous ozone solution. The higher pressure also forces the gas bubbles against the edges 380 further breaking them down into smaller bubbles.

The temperature of the water is also an important consideration in the mass transfer process. At cooler temperatures, the ozone diffuses better in the water. At cooler water temperatures, the contact time between the ozone gas bubbles and the water in forming the aqueous ozone solution is reduced. In general, it is difficult for water to absorb a gas when the water is trying to become a gas. The water from the water supply 330 should be at a temperature of approximately 33° F. to approximately 50° F.

The concentration of the ozone gas in the carrier gas also affects the mass transfer of the ozone gas in to the water. Higher concentrations of ozone in the carrier gas will result in higher concentrations of ozone being absorbed into the aqueous ozone solution. Corona discharge ozone generation equipment generally creates higher concentrations of ozone gas in the carrier gas than ultraviolet types of ozone generation.

Antimicrobial edible films and coatings of aqueous solutions of ozone gas nanobubbles delay or prevent microbial spoilage of food and reduce the risk of surface contamination of food by microorganisms. A nanobubble is a bubble of gas having a diameter of approximately several hundred nanometers or below.

The generation characteristics of ozone gas nanobubbles in aqueous solution may be changed by the dissolved ozone gas concentration in the water of the aqueous solution. The diameters, numbers, and concentration of nanobubbles may be measured by light scattering methods.

The aqueous ozone solution of ozone nanobubbles may be used as cleaning agents both for the prevention of surface fouling and for the de-fouling of surfaces. In particular, the nanobubbles may be used to remove proteins that are already adsorbed to a surface, as well as for the prevention of non-specific adsorption of proteins.

The aqueous ozone solution of ozone nanobubbles may be formed from the processes described herein in which the first aqueous ozone solution is formed and undergoes processing in the reaction vessel 350 and mixing with water to form the second aqueous ozone solution. The processing in the reaction vessel 350 and the mixing with water under pressure reduces the bubble size of the ozone gas into nanobubbles and maintains the ozone gas in the form of nanobubbles.

The first aqueous ozone solution is formed from the venturi 310 injecting ozone gas from the ozone generation skid 200 into water from the water supply 330. The ozone gas in the first aqueous ozone solution forms ozone gas bubbles of a variety of sizes, including macrobubbles of approximately ¼ inch in diameter to approximately 1 inch in diameter. Such macrobubbles of ozone are prone to off-gassing during a cleaning or spraying application.

The first aqueous ozone solution is further processed to reduce the bubble size of the ozone gas. The first aqueous ozone solution is directed to the reaction vessel 350 to reduce bubble size. In the reaction vessel 350, the first aqueous ozone solution is mixed with the pressurized water from the nozzles 360. The macrobubbles of ozone gas in the first aqueous ozone solution are crushed in the reaction vessel 350 against the conical-shaped surface 385 of the reaction vessel 350 by the vortex created by the incoming water from the nozzles 360. The pressure from the incoming water reduces the bubble size of the ozone gas and assists in maintaining the reduced bubble size. The pressure causes the bubbles of ozone gas to shrink.

The second aqueous ozone solution is now formed from the mixing of the water and the first aqueous ozone solution in the reaction vessel 350. The bubbles of the ozone gas in the second aqueous ozone solution have been reduced into nanobubbles. The nanobubbles are nano-sized, ozone gas-containing cavities in the aqueous solution. Essentially all of the ozone gas in the second aqueous ozone solution is contained in nanobubbles of ozone gas dissolved in the second aqueous ozone solution.

The ozone gases in the second ozone solution includes ozone gas bubbles or nanobubbles of approximately 15 nanometers in diameter to approximately 600 nanometers in diameter. Preferably, the second ozone solution includes ozone gas bubbles of approximately 50 nanometers in diameter to approximately 200 nanometers in diameter. The ozone gas bubbles have a wall thickness of approximately 2 nanometers to approximately 60 nanometers. Preferably, the second ozone solution includes ozone gas bubbles having a wall thickness of approximately 5 nanometers in diameter to approximately 20 nanometers in diameter.

The charge density at the surface of the ozone gas bubbles increases as the nanobubbles shrink. The increased charge density at the surface of the nanobubbles promotes self-organization. The increase in charge density promotes longer life and slower diffusion for the ozone gas nanobubbles.

The nanobubbles form a surface tension, which provides for the nanobubbles to adhere to each other. When sprayed onto a contact surface, such as a work surface or other food preparation surface, the adherence between the nanobubbles provides stability and creates a blanket or layer of nanobubbles on the contact surface. The nanobubbles last longer than conventional aqueous ozone solutions. The nanobubbles stop protein from adhering to the contact surface. The nanobubbles remove and prevents bio-fouling The ozone gas solution creates a film, layer or blanket of nanobubbles that may last for several hours to several days on the contact surface. The nanobubbles of ozone gas creates a uniform, dense and longer lasting coating of an aqueous ozone solution. The use of nanobubbles on the contact surface provides an antibacterial layer on the contact surface, which reduces the risk of surface contamination or bio-fouling.

The system 10 produces an aqueous ozone solution to attack and destroy pathogens and act as a no-rinse sanitizer for hard surfaces in a variety of applications, especially industrial processing facilities related to food processing. The solution of aqueous ozone is applied at high pressure to the hard surfaces, and is effective for the removal of soils and bulk materials from the hard surfaces. When applied at high pressure, the solution penetrates the soils and oxides of the biofilm that acts as the bond or glue that allows the soils and oxides to attach themselves to the hard surfaces. The system 10 is designed to be the first totally chemical free system to destroy the biofilm on conveyors systems and hard surfaces during food processing production allowing for continuous or extended production.

There are many applications for both high and low pressure. When the solution discharges from the assembly, the solution could be channeled into both a high pressure stream as well as a low pressure stream. The high-pressure stream of aqueous ozone solution may be better suited for cleaning and sterilizing highly soiled hard surfaces due to the extra force supplied by the high pressure aqueous ozone solution which will help destroy the biofilm adhering the soils to the hard surfaces. The low pressure aqueous ozone solution may be suited for the continuous sanitization of hard surface or application to a food item.

In the embodiment shown, the ozone produced by the ozone generator 240 uses a high electrical discharge called "corona discharge" or "CD". This method is most commonly used to generate usable amounts of ozone for most water treatment applications. Corona discharge creates a small, controlled lightning storm, which involves producing a constant, controlled spark (corona) across an air gap through which a prepared feed gas is passed. This feed gas may be air that has simply had most of its moisture removed or air with enhanced oxygen levels. An important aspect of using the corona discharge methods of ozone production is ensuring that feed gas is dried at the dryer 140 to a dew point of at least approximately −60 F. This is important because as the electrical discharge splits the oxygen molecules, nitrogen molecules are also being split, forming several species of nitrogen oxides, which are normally benign. If feed gas is not sufficiently dried, then the nitrogen oxides combine with moisture from ordinary humidity and form nitric acid, which may be corrosive to the system 10, the hard surfaces, and the industrial facility. Consequently, proper air preparation is important for the operation of the system 10. The relative strength of corona discharge ozone expressed as a percentage of concentration by weight is commonly 0.5-1.7% for systems using dried air, and 1.0-6.0% when an oxygen enhanced feed gas is used.

A properly installed and operated system 10 poses no health hazards. While ozone is a toxic gas and the established concentration limits must be adhered to, the odor threshold of 0.01 ppm is far below the safety limit of 0.1 ppm exposure over an eight hour period. The first symptoms of excessive ozone exposure are headaches, eye, nose or throat irritation or a shortness of breath. These symptoms can be relieved by the simple application of fresh air. While no deaths have been reported from ozone, sound safety practices deserve attention. Ozone off-gas containment and destruction equipment for most water treatment applications is readily available and is usually a simple device containing either activated carbon or manganese dioxide.

Ozone is a much more powerful oxidizer than chlorine. Based on EPA charts of surface water CT values (disinfectant residual and time constant), chlorine CT values are nearly 100 times greater than ozone, meaning that ozone acts much more quickly than chlorine. Ozone creates none of the trihalomethanes commonly associated with chlorine compounds and properly matched to the application; ozone will reduce most organic compounds to carbon dioxide, water and a little heat. Finally, as ozone sheds the atom of the oxygen causing its molecular instability during the oxidation process, it becomes oxygen again.

Facilities processing bottled water, perishable goods (meat, seafood, fruit, vegetables, etc.) are examples of ideal applications for the system 10. The fact that ozone efficiently oxidizes the organics that cause taste, odor, and color problems without leaving a high residual helps to simplify many water treatment. The lack of residual from ozone cleaning and sanitation also makes ozone perfect for pre- and post-treatment processes in wash pad recycle systems, where the use of a chlorine compound would contribute to pH control or off gas problems. Additionally, ozone oxidizes and precipitates many metals and destroys some pesticides without leaving a trace. Finally, ozone functions as a preoxidizer of iron, manganese and sulfide compounds, allowing for their removal by simple direct filtration. Ozone acts quickly and easily, and the water quality resulting from its use is unmatched.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

What is claimed is:

1. A method of producing an aqueous ozone solution for supplying an industrial cleaning system with the aqueous ozone solution, comprising:
   injecting ozone gas into water to form a first aqueous ozone solution, wherein the first aqueous ozone solution comprises ozone gas dissolved in the water;
   mixing the first ozone solution with additional fresh water to form a second ozone solution;
   processing the second ozone solution, by the mixing of the first ozone solution with additional water, to reduce a bubble size of ozone gas dissolved in the second ozone solution, wherein the second ozone solution comprises the ozone gas in nanobubbles of ozone gas dissolved in the second ozone solution; and,
   directing the second ozone solution to an industrial cleaning system, wherein the second ozone solution provides a cleaning or sterilizing fluid for the industrial cleaning system.

2. The method of producing an aqueous ozone solution for supplying an industrial cleaning system according to claim 1, wherein the processing occurs under pressure.

3. The method of producing an aqueous ozone solution for supplying an industrial cleaning system according to claim 1, wherein an oxidation reduction potential value for the first aqueous ozone solution is approximately the same as an oxidation reduction potential value for the second aqueous ozone solution.

4. The method of producing an aqueous ozone solution for supplying an industrial cleaning system according to claim 1, wherein the second aqueous ozone solution has an oxidation reduction potential of up to approximately 2.6.

5. The method of producing an aqueous ozone solution for supplying an industrial cleaning system according to claim 1, wherein the second aqueous ozone solution has an ozone concentration of up to approximately 20 ppm.

6. The method of producing an aqueous ozone solution for supplying an industrial cleaning system according to claim 1, further comprising mixing the additional fresh water with the first aqueous ozone solution in a reaction vessel, and then directing the second ozone solution to a contact tank.

7. The method of producing an aqueous ozone solution for supplying an industrial cleaning system according to claim 1, wherein the nanobubbles have an average diameter of approximately 15 nanometers to approximately 600 nanometers.

8. The method of producing an aqueous ozone solution for supplying an industrial cleaning system according to claim 1, wherein the nanobubbles have an average diameter of approximately 50 nanometers to approximately 200 nanometers.

9. The method of producing an aqueous ozone solution for supplying an industrial cleaning system according to claim 1, wherein the nanobubbles have a wall thickness of approximately 2 nanometers to approximately 60 nanometers.

10. The method of producing an aqueous ozone solution for supplying an industrial cleaning system according to claim 1, wherein the second aqueous ozone solution is formed in a ratio of approximately 1 part by volume of the additional fresh water from the water supply with approximately 4 parts by volume to approximately 9 parts by volume of the first aqueous ozone solution.

11. A method of producing an aqueous ozone solution to supply an industrial cleaning application, comprising:
   injecting ozone gas into water to form a first aqueous ozone solution, wherein the first aqueous ozone solution comprises ozone gas dissolved in the water, and the ozone gas form bubbles in the water having an average diameter of approximately 0.25 inches to approximately 1.0 inches;

mixing the first aqueous ozone solution with additional fresh water to form a second aqueous ozone solution;

processing the second aqueous ozone solution by the mixing of the first ozone solution with the additional fresh water in a reaction vessel, wherein, after the processing, the second aqueous ozone solution comprises the ozone gas in nanobubbles of ozone gas dissolved in the second aqueous ozone solution, wherein the nanobubbles have an average diameter of approximately 15 nanometers to approximately 600 nanometers; and, supplying an industrial cleaning system with the second aqueous ozone solution.

12. The method of producing an aqueous ozone solution to supply in an industrial cleaning application according to claim 11, further comprising mixing the water with the first aqueous ozone solution in a reaction vessel, and breaking the bubbles of ozone gas in the first aqueous ozone solution against surfaces of the reaction vessel into the nanobubbles of the second aqueous ozone solution.

13. The method of producing an aqueous ozone solution to supply in an industrial cleaning application according to claim 11, wherein an oxidation reduction potential value for the first aqueous ozone solution is approximately the same as an oxidation reduction potential value for the second aqueous ozone solution.

14. The method of producing an aqueous ozone solution to supply in an industrial cleaning application according to claim 11, wherein the nanobubbles have an average diameter of approximately 50 nanometers to approximately 200 nanometers.

* * * * *